United States Patent [19]

Tamés

[11] Patent Number: 4,457,909

[45] Date of Patent: Jul. 3, 1984

[54] ORAL RINSE FORMULATION AND METHOD OF TREATING MOUTH AND THROAT IRRITATIONS THEREWITH

[76] Inventor: Tamés, 509 Matador La., Charlotte, N.C. 28209

[21] Appl. No.: 424,188

[22] Filed: Sep. 27, 1982

[51] Int. Cl.$^3$ ............... A61K 7/24; A61K 33/14; A61K 31/375

[52] U.S. Cl. .................... 424/55; 424/49; 424/57; 424/153; 424/280

[58] Field of Search ............... 424/49–58, 424/153, 280

[56] References Cited

U.S. PATENT DOCUMENTS

| | | | |
|---|---|---|---|
| 1,753,531 | 4/1930 | Prince | 424/95 |
| 1,817,664 | 8/1931 | Badanes | 424/49 |
| 1,968,858 | 8/1934 | Sheffield et al. | 424/49 |
| 2,124,971 | 7/1938 | Eisenberg et al. | 424/55 |
| 2,224,252 | 10/1940 | Callaway | 426/590 |
| 2,470,906 | 5/1949 | Taylor | 424/49 |
| 2,623,002 | 12/1952 | Fricke | 424/280 |
| 2,658,851 | 11/1953 | Brandenberger | 424/153 |
| 2,798,023 | 7/1957 | Berger | 424/280 |
| 2,811,483 | 10/1957 | Aterno et al. | 424/280 |
| 2,816,854 | 12/1957 | Gross | 424/280 |
| 2,994,642 | 8/1961 | Bossard | 424/49 |
| 3,065,139 | 11/1962 | Ericsson et al. | 424/280 |
| 3,306,824 | 2/1967 | Laasko et al. | 424/280 |
| 3,337,404 | 8/1967 | Polli et al. | 424/153 |
| 3,657,424 | 4/1972 | Atkins et al. | 424/153 |
| 3,676,553 | 7/1972 | Reynolds | 424/153 |
| 3,689,636 | 9/1972 | Svajda | 424/153 |
| 3,886,265 | 5/1975 | Evers et al. | 424/49 |
| 3,975,514 | 8/1976 | Weisz | 424/52 |
| 4,042,684 | 8/1977 | Kahm | 424/153 |
| 4,213,961 | 7/1980 | Curtis et al. | 424/55 |
| 4,322,407 | 3/1982 | Ko | 424/153 |

FOREIGN PATENT DOCUMENTS

| | | | |
|---|---|---|---|
| 113643 | 8/1941 | Australia | 424/280 |
| 1922653 | 11/1970 | Fed. Rep. of Germany | 424/280 |
| 2312M | 2/1964 | France | 424/280 |
| 3643M | 10/1965 | France | 424/280 |
| 7513892 | 6/1977 | Netherlands | 424/280 |
| 486055 | 5/1938 | United Kingdom | 424/280 |
| 503476 | 3/1939 | United Kingdom | 424/280 |
| 1135643 | 12/1968 | United Kingdom | 424/280 |
| 2052986A | 2/1981 | United Kingdom | 424/280 |

*Primary Examiner*—Shep K. Rose
*Attorney, Agent, or Firm*—Richards, Shefte & Pinckney

[57] ABSTRACT

A formulation of a mixture of a salt, preferably sodium chloride, and ascorbic or isoascorbic acid, when mixed in proportions by weight of 90–92% salt and 8–10% acid and dissolved in a volume of water providing a solution concentration (weight per unit volume) of 4–6% salt and 0.3–0.6% acid provides an effective oral rinse useful in bathing and cleansing mouth and throat tissues to relieve and prevent mouth and throat irritations which accompany colds, influenza and periodontal disease.

18 Claims, No Drawings

ORAL RINSE FORMULATION AND METHOD OF TREATING MOUTH AND THROAT IRRITATIONS THEREWITH

BACKGROUND OF THE INVENTION

The present invention relates to the treatment of mouth and throat irritations and particularly to formulations for oral rinsing and methods therefor.

Sore throat, laryngitis, mouth and throat ulcers, excessive mucus and other mouth and throat irritations typically accompany common colds, influenza and like ailments and, as is well known, no cure or dependable preventative exists for such ailments. In recent years, Vitamin C (ascorbic acid) has come into routine and widespread dietary use as an alleged preventative or mitigant of the common cold, influenza and their manifestations. Although Vitamin C is known to be an essential nutrient in the human diet helping to maintain the integrity of connective tissues, the osteoid tissue of bone and the dentin of teeth, its precise mechanism of action in the human body is unknown and no accepted medical proof as yet exists for the claimed preventative effect on colds and influenza of the regular ingestion of Vitamin C. When a cold or influenza is contracted, mouthwashing and gargling is an accepted treatment for the accompanying symptoms and various commerical mouthwashes and gargles are available for this purpose. In this latter regard, it is also known that a simple aqueous solution of common table salt (sodium chloride) may be used as a mouthwash and gargle for the treatment of such cold symptoms.

Apart from the mouth and throat irritations symtomatic of colds, inflammation of the supportive tissues of the teeth typically accompanies periodontal disease which may result in the loosening and loss of teeth and, in fact, periodontal disease now ranks as the major cause of the loss of teeth in adults of middle age and older. Relatively little is known of the particular mechanism by which this disease develops and progresses, but the formation of plaque on the teeth in the region of the supportive gum tissues, particularly the gingival crevises, is known to cause inflammatory reactions with attendant swelling, redness, cellular exudate and bacterial growth, and it is generally considered such conditions are necessary for the development of periodontal disease. Historically, the only conventionally recognized aid in preventing periodontal disease is the maintenance of a regular routine of oral hygiene, particularly periodic toothbrushing and the use of dental floss to remove food particles and plaque from between the teeth and below the gum line. However, with the introduction in recent years of water irrigation devices adapted to produce a stream of water for use in flushing around the teeth and gums, water irrigation has been proposed and come into use as a method of preventing periodontal disease.

While Vitamin C and mouthwashes have in the past been conventionally understood to have separate and distinct uses in differing manners in the avoidance of common colds, Vitamin C being considered to be useful as a cold preventative when regularly ingested and metabolized by the body and mouthwashes being considered to be a useful oral treatment of various cold symptoms when contracted, it has now been discovered that an aqueous solution of a mixture of Vitamin C or its related compound erythorbic acid (isoascorbic acid) and common table salt or another similar salt is of significant effectiveness as a mouthwash and gargle in the prevention, treatment and relief of mouth and throat irritations resulting from colds. Additionally, although ordinary water is primarily recommended for use in mouth irrigation, it has been discovered that such an aqueous solution may be advantageously employed with conventional water irrigation devices as a flushing medium effective to remove plaque, prevent its formation and generally promote the health of the supportive tissues of the teeth. It is accordingly an object of the present invention to provide a formulation of one or more such acid and salt components which is suitable for appropriate regular use as an oral rinse, either by mouthwashing, gargling or mouth irrigation, to aid in the prevention, treatment and relief of colds, influenza and certain of their symptoms, and in the prevention and treatment of periodonal disease and the promotion of periodontal health.

SUMMARY OF THE INVENTION

Briefly described, the present invention in its broad aspects provides a formulation useful in aqueous solution as an oral rinse, the formulation comprising at least one water-soluble salt selected from the group consisting of the citrates, tartrates, ascorbates, chlorides, iodides, bromides, fluorides, sulfates, and phosphates of metals of the group of sodium, potassium, lithium, magnesium, and calcium, and at least one acid component selected from the group consisting of ascorbic acid and erythorbic acid. With the present formulation, a new method of preventing and treating mouth and throat irritations is provided by orally rinsing with the aforedescribed formulation. For purposes of the present application, the term "oral rinse" is used herein to designate the usability of a liquid formulation for any activity involving the bathing or cleansing of the tissues of the mouth, including but not limited to mouthwashing, gargling, and mouth irrigation, and the terms "rinsing" and "orally rinsing" are used to designate such activities.

In its preferred form, the formulation constitutes a mixture of either sodium chloride alone or a mixture thereof with potassium chloride as the salt component and ascorbic acid as the acid component. The formulation may be prepared in granulated or powdered solid form as a homogeneous mixture or in an aqueous solution. In solid form, the concentration of the salt is preferably between approximately 90% and approximately 99.5% by weight and the concentration of the acid is preferably between approximately 0.5% and approximately 10% by weight. In liquid form, the concentration of the salt is preferably between approximately 3% and approximately 7% weight per unit volume and the concentration of the acid is preferably between approximately 0.01% and approximately .7% weight per unit volume. A suitable stabilizing agent or agents, such as propylene glycol, glycerol, ethylenediaminetetraacetic acid, or methyl paraben, is preferably added in the liquid form to prevent degradation of the acid component. Also, a flavoring agent and a coloring agent may be added.

DESCRIPTION OF THE PREFERRED EMBODIMENT

The preferred embodiment of the formulation of the present invention is a mixture of one or more water-soluble salts and either or both of the acids of ascorbic acid or erythorbic acid (isoascorbic acid) in the concentrations hereinafter indicated. The salts which have been found to be useful are the citrates, tartrates, ascorbates, chlorides, iodides, bromides, fluorides, sulfates and phosphates of the metals sodium, potassium, lithium, magnesium, and calcium. In practice, sodium chloride and potassium chloride, either alone or as a mixture thereof, have been found to be particularly effective and are preferred. Ascorbic acid has been found to be of greater effectiveness than the similar but less active erythorbic acid and is preferred thereover. All of these acceptable components are readily available in quantity through commercial sources.

In one embodiment, the formulation is prepared in solid form as a granulated or powdered homogeneous mixture of the salt and acid components. The aforementioned acceptable components are available in such form and may accordingly be mechanically blended into the desired solid form mixture using conventional equipment such as a powder blending machine. In this embodiment, the salt is employed in a concentration by weight of between approximately 90% and approximately 99.5% and the acid is employed in a concentration by weight of between approximately 0.5% and approximately 10%. Preferably, the salt is employed in the lower range of its permissible concentrations between approximately 90% and 92% by weight and the acid is employed in the upper range of its permissible concentrations between approximately 8% and 10% by weight. The following are representative examples of preferred formulations:

| Component | Weight |
|---|---|
| Formulation A | |
| Sodium Chloride | 90 gram |
| Ascorbic Acid | 10 gram |
| | 100 gram |
| Formulation B | |
| Sodium Chloride | 92 gram |
| Ascorbic Acid | 8 gram |
| | 100 gram |
| Formulation C | |
| Sodium Chloride | 45 gram |
| Potassium Chloride | 45 gram |
| Ascorbic Acid | 10 gram |
| | 100 gram |
| Formulation D | |
| Sodium Chloride | 46 gram |
| Potassium Chloride | 46 gram |
| Ascorbic Acid | 8 gram |
| | 100 gram |

Such solid formulations will be understood by those skilled in the art to be relatively stable and will so remain for indefinite periods of time if manufactured using anhydrous ingredients and packaged by appropriate means protecting the formulations from moisture, air and light. It is contemplated that the solid formulations would be most advantageously packaged in small quantities suitable for individual use, for instance in small, hermetically sealed foil packets each containing between approximately eight and twelve gram of the formulation. In preferred use of such solid formulations, between approximately eight and twelve gram thereof (one individual package) is dissolved in approximately 6 ounces (177 milliliters) of water, preferably warm water between 90° F. and 110° F., and is immediately used as an oral rinse to bathe and cleanse the surface tissues within the mouth and throat. The following are representative examples of such solutions of the above preferred solid Formulations A-D prepared by dissolving 10 gram of each thereof in respective 6 ounce quantities of water:

| Component | Weight | % Concentration (gram per 100 milliliter) |
|---|---|---|
| Formulation A | | |
| Sodium Chloride | 9 gram | 4.81 gram |
| Ascorbic Acid | 1 gram | .53 gram |
| Water | 177 milliliters (177 gram) | 100.0 milliliter |
| Formulation B | | |
| Sodium Chloride | 9.2 gram | 4.91 gram |
| Ascorbic Acid | 0.8 gram | .43 gram |
| Water | 177 milliliter | 100.0 milliliter |
| Formulation C | | |
| Sodium Chloride | 4.5 gram | 2.41 gram |
| Potassium Chloride | 4.5 gram | 2.41 gram |
| Ascorbic Acid | 1.0 gram | .53 gram |
| Water | 177 milliliter | 100.0 milliliter |
| Formulation D | | |
| Sodium Chloride | 4.6 gram | 2.46 gram |
| Potassium Chloride | 4.6 gram | 2.46 gram |
| Ascorbic Acid | .8 gram | .43 gram |
| Water | 177 milliliter | 100.0 milliliter |

In another embodiment, the formulation is prepared and packaged in liquid form as an aqueous solution of the aforedescribed solid formulation. It is contemplated that the formulation in this embodiment is most preferably prepared in the concentration preferred for its end use, for instance in the solution concentration noted above. More specifically, the salt is employed in a solution concentration of between approximately 3% and approximately 7% weight per unit volume, preferably between approximately 4% and 6%, and the acid is employed in a solution concentration of between approximately 0.01% and approximately 0.7%, preferably between approximately 0.3% and 0.65%. (As used herein, the term weight per unit volume is intended to carry its ordinary meaning in the art, i.e. grams per 100 milliliters.) The above set forth examples of solutions of solid Formulations A-D are representative of this embodiment, but liquid formulations according to this embodiment would preferably be produced on a significantly larger scale, e.g. by dissolving the entire quantity of any one of solid Formulations A-D in sixty ounces (1.77 liters) of water. Alternatively, it is contemplated that the liquid formulation in this embodiment may be prepared and packaged in a concentrated form having a substantially greater solution concentration of the salt and acid components than is preferred for ultimate use as an oral rinse, which concentrated solution would accordingly be diluted in small amounts when used.

Either of the diluted or concentrated liquid formulations would preferably be packaged in appropriate containers suitable to hermetically seal the formulation from mositure, air and light, for instance in glass or plastic bottles. As those skilled in the art will understand, the acid in either liquid formulation is nevertheless subject to degradation over time and, accordingly, it is preferred that distilled water be employed as the solvent and further that a suitable water-soluble stabilizing agent be added to the solution to prevent the degradation of the acid. Various stabilizing agents suitable for this purpose are known in the prior art, any of which may be employed. It has been found that one or more of propylene glycol, glycerol, ethylenediaminetetraacetic acid (EDTA), and methyl paraben are well suited for such purpose in the present liquid formulations. Additionally, since the salty taste of the liquid formulations may be considered unpleasant by some people, it is contemplated that a conventional flavoring additive may be added to the formulations. For this purpose, peppermint, wintergreen, orange, lime, cherry, strawberry, cinnamon, clove and anise flavorings have been acceptably employed in various conventional mouthwashes and gargles and would be satisfactory for use in the present formulation. A conventional coloring agent may also be added. The following are representative examples of preferred solid and aqueous formulations suitable for commercial manufacture:

| Component | Weight |
|---|---|
| Solid Formulation E | |
| Sodium Chloride, fine granular (dry) | 44.400 gram |
| Potassium Chloride, fine granular (dry) | 44.000 gram |
| Tricalcium phosphate, fine granular (dry) | 1.199 gram |
| Ascorbic Acid, U.S.P. fine granular | 10.000 gram |
| Peppermint oil | 0.400 gram |
| FD & C Blue No. 1 | 0.001 gram |
| | 100.000 gram |
| Liquid Formulation F | |
| Sodium Chloride | 2.50 gram |
| Potassium Chloride | 2.40 gram |
| Sodium Ascorbate | 0.10 gram |
| Ascorbic Acid | 0.50 gram |
| Glycerol | 3.00 gram |
| EDTA | 0.01 gram |
| FD & C Blue No. 1 | as desired |
| Flavoring Agent | as desired |
| Distilled Water | to yield 100 milliliter total formulation |

As previously noted, each of the embodiments of the present formulation, once appropriately prepared as necessary in the proper solution concentrations specified for use, is employed as an oral rinse in any appropriate manner to bathe and cleanse the surface tissues in the mouth and throat. Through the inventor's personal use in mouthwashing and gargling with the present formulation and comparative use of formulations of a salt solution alone and an ascorbic acid solution alone, the present formulation has been observed and considered to provide noticeably greater relief from the dryness and pain associated with sore throat and other mouth and throat irritations and to speed the recovery therefrom more readily than either of the other formulations. It is believed that these effects result from the production by the present formulation of a bacteriostatic effect on bacteriae, virus, germs and the like in the mouth and throat coupled with an osmotic effect on the mucous membranes of the mouth and throat which stimulates and promotes the flow of mucus and saliva aiding in the washing away and removal of such bacteriae and the like, and it is not believed that either a formulation of a salt solution alone or a formulation of an ascorbic acid solution alone is capable of producing all such results. It is recommended that the present formulation be so used as a gargle on a regular, daily basis as a routine part of a program of personal oral hygiene, it being believed that such routine use of the formulation producing the above effects on a regular basis will significantly aid in the prevention of colds and influenza and their symptoms. Further, through the inventor's personal use of the present formulation for mouth irrigation using a conventional irrigation device and comparative use of water alone for such purpose, the present formulation has been observed to more effectively remove plaque from the teeth and to aid in preventing its accumulation and it is recommended that the present formulation also be periodically employed for mouth irrigation.

The present invention has been described in detail above for purposes of illustration only and is not intended to be limited by this description or otherwise to exclude any variation or equivalent arrangement that would be apparent from, or reasonably suggested by the foregoing disclosure to the skill of the art.

I claim:

1. A soluble solid mouthwash formulation adapted to be dissolved in water for use as an oral bathing and cleansing rinse by gargling, mouthwashing, oral irrigation and the like for the prevention and treatment of sore throat and mouth and throat ulcers and like irritations, for the control of dental plaque and for other routine oral hygenic uses, said formulation consisting essentially of a powdered homogeneous mixture of at least one water soluble inorganic salt selected from the group consisting of sodium chloride and potassium chloride in a total concentration in the range of approximately 90% to 92% by weight, and ascorbic acid in a concentration in the range of approximately 8% to 10% by weight.

2. The soluble solid mouthwash formulation of claim 1 and characterized further in that said inorganic salt is a mixture of sodium chloride and potassium chloride in generally the same concentrations by weight.

3. The soluble solid mouthwash formulation of claim 2 and characterized further by tricalcium phosphate in a concentration in the range of approximately 1% by weight to act as a buffer to elevate the overall pH of the formulation when in solution and to prevent caking of the powdered formulation for improving its flowability.

4. The soluble solid mouthwash formulation according to claim 3 and characterized further by a flavoring additive and a coloring agent in substantially small concentrations by weight.

5. The soluble solid mouthwash formulation according to claim 4 and characterized further in that the concentration of sodium chloride is approximately 44.4% by weight, the concentration of potassium chloride is approximately 44.0% by weight, the concentration of tricalcium phosphate is approximately 1.199% by weight, the concentration of ascorbic acid is approximately 10.0% by weight, the concentration of the flavoring additive is approximately 0.4% by weight, and the concentration of the coloring agent is approximately 0.001% by weight.

6. The soluble solid mouthwash formulation of claim 1 and characterized further in that said inorganic salt is sodium chloride.

7. The soluble solid mouthwash formulation of claim 6 and characterized further by tricalcium phosphate in a concentration in the range of approximately 1% by weight to act as a buffer to elevate the overall pH of the formulation when in solution and to prevent caking of the powdered formulation for improving its flowability.

8. The soluble solid mouthwash formulation of claim 7 and characterized further by a flavoring additive and a coloring agent in substantially small concentrations by weight.

9. The liquid mouthwash formulation consisting essentially of the solid formation of claim 1 in aqueous solution in a concentration of one to ten parts of the solid formulation by weight to one hundred parts of water by weight.

10. A liquid mouthwash formulation adapted for use as an oral bathing and cleansing rinse by gargling, mouthwashing, oral irrigation and the like for the prevention and treatment of sore throat and mouth and throat ulcers and like irritations, for the control of dental plaque and for other routine oral hygenic uses, said formulation consisting essentially of an aqueous solution in distilled water of at least one water soluble inorganic salt selected from the group of sodium chloride and potassium chloride in a total concentration by weight per unit volume in the range of approximately 5.0 grams per 100 milliliters, ascorbic acid in a weight per unit volume concentration in the range of approximately 0.50 grams per 100 milliliters, and at least one water soluble stabilizing agent to prevent degradation of the ascorbic acid 11. The liquid mouthwash formulation of claim 10 and characterized further in that said inorganic salt is a mixture of sodium chloride and potassium chloride in generally the same concentrations by weight per unit volume.

12. The liquid mouthwash formulation of claim 11 and characterized further by sodium ascorbate in a concentration in the range of approximately 0.10 grams per 100 milliliters to act as a buffer to elevate the overall pH of the formulation.

13. The liquid mouthwash formulation according to claim 12 and characterized further by a flavoring additive and a coloring agent in substantially small concentrations by weight per unit volume.

14. The liquid mouthwash formulation according to claim 13 and characterized further in that the concentration of sodium chloride is approximately 2.50 grams per 100 milliliters, the concentration of potassium chloride is approximately 2.40 grams per 100 milliliters, the concentration of sodium ascorbate is approximately 0.10 grams per 100 milliliters, the concentration of ascorbic acid is approximately 0.50 grams per 100 milliliters, and the concentration of the stabilizing agent is approximately 3.0 grams per 100 milliliters.

15. The liquid mouthwash formulation according to claim 10 and characterized further in that said inorganic salt is sodium chloride.

16. The liquid mouthwash formulation according to claim 15 and characterized further by sodium ascorbate in a concentration in the range of approximately 0.10 grams per 100 milliliters to act as a buffer to elevate the overall pH of the formulation.

17. The liquid mouthwash formulation according to claim 16 and characterized further by a flavoring additive and a coloring agent in substantially small concentrations by weight per unit volume.

18. A process for bathing and cleansing the mouth for the prevention and treatment of sore throat and mouth and throat ulcers and like irritations, for the control of dental plaque and for other routine oral hygenic uses, said process consisting essentially of providing a liquid mouthwash formulation consisting essentially of an aqueous solution in distilled water of at least one water soluble inorganic salt selected from the group of sodium chloride and potassium chloride in a concentration by weight per unit volume in the range of approximately 5.0 grams per 100 milliliters, and ascorbic acid in a weight per unit volume concentration in the range of approximately 0.50 grams per 100 milliliters, orally rinsing the teeth, gums and other mouth and throat surfaces by gargling, mouthwashing, orally irrigating or the like with a quantity of said liquid mouthwash formulation for bacteriostatically attacking at least some bacteriae, germs and the like on said surfaces, for loosening and washing away at least some said bacteriae, germs and the like, and for osmotically penetrating the mucous membranes of said gums, mouth and throat surfaces for stimulating and enhancing mucus and saliva flow as an aid to said loosening and washing away and for at least some absorption of said ascorbic acid in said mucous membranes, and thereafter expectorating said quantity of said formulation.

* * * * *

UNITED STATES PATENT OFFICE
CERTIFICATE OF CORRECTION

Patent No. 4,457,909  Dated July 3, 1984

Inventor(s) Theobaldo Tames

It is certified that error appears in the above-identified patent and that said Letters Patent are hereby corrected as shown below:

On the title page

The _full_ name of the inventor should appear as follows:

--Theobaldo Tames--

Signed and Sealed this

Eighteenth Day of February 1986

[SEAL]

Attest:

DONALD J. QUIGG

Attesting Officer    Commissioner of Patents and Trademarks